United States Patent [19]

Entani et al.

[11] Patent Number: 4,654,306

[45] Date of Patent: Mar. 31, 1987

[54] **NOVEL BACTERIUM, *ACETOBACTER ALTOACETIGENES* MH-24, USEFUL FOR THE FERMENTATION PRODUCTION OF VINEGAR**

[75] Inventors: Etsuzo Entani, Handa; Seiichi Fujiyama; Shoji Ohmori, both of Aichi; Hiroshi Masai, Handa, all of Japan

[73] Assignee: Nakano Vinegar Co., Ltd., Handa, Japan

[21] Appl. No.: 703,705

[22] Filed: Feb. 21, 1985

[30] Foreign Application Priority Data

Feb. 28, 1984 [JP] Japan .................................. 59-35327

[51] Int. Cl.$^4$ ........................... C12N 1/20; C12R 1/02
[52] U.S. Cl. ..................................... 435/253; 435/823
[58] Field of Search ................................ 435/823, 253

[56] References Cited

U.S. PATENT DOCUMENTS 4,514,563  4/1985  Fujiyama et al. ................... 435/101

OTHER PUBLICATIONS

*Agricultural Biological Chemistry*, vol. 48, No. 10, (1984), pp. 2405–2414.
*Agricultural Biological Chemistry*, vol. 44, No. 12, (1980), pp. 2901–2906.

Primary Examiner—Charles F. Warren
Assistant Examiner—Rebecca L. Thompson
Attorney, Agent, or Firm—Frishauf, Holtz, Goodman & Woodward

[57] ABSTRACT

A novel species of acetic acid bacteria belonging to the genus of Acetobacter, to which a scientific name of Acetobacter altoacetigenes MH-24 (FERM BP-491) is given. The bacteria can grow in a culture medium containing at least 4 w/v % of acetic acid with a pH of 3.5 at the highest. Pure samples of species have been isolated and used for the fermentation production of vinegar without undertaking the conventional inoculation process using the prior art seed vinegar to provide a high-quality vinegar of high acetic acid concentration such as white vinegar, with high production efficiency.

1 Claim, No Drawings

NOVEL BACTERIUM, ACETOBACTER ALTOACETIGENES MH-24, USEFUL FOR THE FERMENTATION PRODUCTION OF VINEGAR

BACKGROUND OF THE INVENTION

The present invention relates to a novel species of bacterium useful in acetic acid fermentation and, more particularly, to a novel species of bacterium named *Acetobacter altoacetigenes* useful in the fermentative production of vinegars of high acetic acid concentration such as white vinegar.

In the fermentation production of vinegars having a high acetic acid concentration such as white vinegar and the like, it is generally understood in the prior art that the acetic acid bacteria used in the fermentation could not be isolated and stored. The fermentation production of such a vinegar is usually performed by the so-called inoculation process using seed vinegar, in which a portion of the fermentation liquid after completion of the fermentation or a portion of the fermenting broth, which contains the acetic acid bacteria, is used to inoculate the next batch of starting materials.

The acetic acid bacteria of the seed vinegar which have activity for producing a high concentration of acetic acid rapidly die so that the fermentation liquid after completion of the fermentation and/or a large volume of the fermenting broth is required for seed vinegar. A pure culture of the acetic acid bacterium is difficult to obtain in such an inoculation process and decrease in the productivity is sometimes unavoidable in the acetic acid production due to contamination with noxious bacteria so that the fermentation must be performed under complicated process control conditions.

SUMMARY OF THE INVENTION

It is an object of the present invention to provide a species of acetic acid bacterium having activity for producing acetic acid in a fermentation process with high productivity. The said bacterium is suitable for isolation and storage of the purified bacterium.

Another object of the invention is to provide a means for the storage of the acetic acid bacterium without the use of the prior art seed vinegar which involves the aforenoted problems and disadvantages.

The bacterium obtained by isolation from a fermenting broth as a result of the extensive investigations by the inventors including the bacteriological examination of the taxonomic characteristics has been identified as the genus Acetobacter and is a novel species not described in any prior literatures.

This novel species of the genus Acetobacter has been named as *Acetobacter altoacetigenes*. The stock of a typical strain, *Acetobacter altoacetigenes* MH-24, has been deposited at the Fermentation Research Institute, Agency of Industrial Science and Technology, Ministry of International Trade and Industry; and assigned deposition No. FERM BP-491 (referred to hereinafter as MH-24).

A pure culture of this novel acetic acid bacterium (MH-24) was used as the seed in the fermentation production of white vinegar which has a high acetic acid concentration to produce a white vinegar having a high acetic acid concentration and having excellent flavor and taste. The fermentation proceeded with high stability. Frothing did not take place in the course of the fermentation thereby facilitating control of the fermentation process.

DETAILED DESCRIPTION OF THE PREFERRED EMBODIMENTS

A description of the procedure for the isolation of the acetic acid bacterium M-24 follows:

An agar plate medium, referred to as AE agar plate, was prepared by thinly coating a soft agar medium which contains 0.2 w/v % of yeast extract, 0.3 w/v % of polypeptone, 1.5 w/v % of glucose, 6.5 w/v % of acetic acid, 2 v/v % of ethyl alcohol and 0.5 w/v % of agar, with another medium having the same composition as above except that the agar content was 1 w/v %. A vinegar fermention broth was streaked on the surface of the AE agar and culture was performed in an incubator controlled at a constant temperature of 30° C. and under a constant relative humidity of 95 to 100% for 7 to 30 days to obtain bacterial colonies which were processed using the procedure of single-colony isolation repeatedly to isolate the bacterium MH-24 in a pure state.

The thus isolated bacteria were found to belong to a novel species of the genus Acetobacter and the species was given a scientific name of *Acetobacter altoacetigenes*.

The bacteriological properties follow:

(a) Morphological characteristics after 10 days culture in an incubator at a temperature of 30° C. with a relative humidity of 95 to 100%

1. Shape and size: rods, 0.5 $\mu$m $\times$ 0.8–1.3 $\mu$m, rarely including curved and filamentous cells
2. Population: single or pair
3. Motility: none
4. Flagella: none
5. Spores: none
6. Gram staining: negative
7. Acid-fasteners: negative (b) Cultural characteristics on various culture media 1. Nutrient agar plate: no growth
2. Nutrient agar slant: no growth
3. Nutrient broth: no growth
4. Nutrient gelatin stab culture: no growth and no liquefaction
5. Litmus milk: no changes
6. AE agar plate: slow growing but moderate growth, smooth surface, light gray to light brown in color, small, punctiform colonies
7. AE broth (a liquid medium prepared with the same composition as the AE agar plate except that the agar was omitted): weak growth to produce turbidity in the culture by shaking or agitation with aeration but no growth by standing (c) Physiological characteristics, as tested with the AE agar plate and AE broth as the basal media if not otherwise mentioned below 1. Nitrate reduction: negative
2. Denitrification: negative
3. VP test: negative
4. Formation of indole: negative
5. Formation of hydrogen sulfide: negative
6. Hydrolysis of starch: negative
7. Utilization of citric acid in Koser's and Christensen's media: negative 8. Utilization of inorganic nitrogen sources, nitrates: negative Ditto, amonium salts: negative
9. Formation of pigment: negative
10. Urease: negative
11. Oxidase: negative
12. Catalase: positive
13. Oxygen requirement: obligatory aerobic
14. pH range for growth: pH 2.2 to pH 3.5 (The pH of the AE agar plate was adjusted by use of sodium hydroxide and hydrochloric acid. When the pH was adjusted by use of hydrochloric or phosphoric acid and sodium hydroxide with omission of acetic acid, no growth took place even at a pH within the above range.)
15. Temperature range for growth: 15° to 35° C.
16. Vitamin requirement: positive
17. Range of acetic acid concentration for growth: 4–10 w/v %
18. Assimilation of carbon sources
Tests for the following compounds (1) to (22) were undertaken each by use of an AE agar plate devoid of glucose for (1), (2) and (4) through (15) and an AE agar plate devoid of ethyl alcohol for (17) through (22).
   (1) L-Arabinose: —
   (2) D-Xylene: —
   (3) D-Glucose: +
   (4) D-Mannose: —
   (5) D-Fructose: +
   (6) D-Galactose: —
   (7) Maltose: —
   (8) Sucrose: +
   (9) Lactose: —
   (10) Trehalose: —
   (11) D-Sorbitol: +
   (12) D-Mannitol: +
   (13) Inositol: —
   (14) Glycerol: —
   (15) Starch: —
   (16) Ethyl alcohol: +
   (17) n-Propyl alcohol: +
   (18) iso-Propyl alcohol: +
   (19) n-Butyl alcohol: —
   (20) iso-Butyl alcohol: —
   (21) n-Amyl alcohol: —
   (22) iso-Amyl alcohol: —
19. Oxidation of ethyl alcohol (acetic acid formation in AE broth): positive
20. Overoxidation of ethyl alcohol (decrease of formed acetic acid in AE broth): negative
21. Assimilation of acetic acid (decrease of acetic acid in AE broth culture medium): negative
22. Decomposition of acetic acid (oxygen consumption for acetic acid and alkalinization of acetates): negative
23. Assimilation of lactic acid (growth in AE broth with replacement of acetic acid with lactic acid and decrease of lactic acid in an AE broth with addition of lactic acid): negative
24. Decomposition of lactic acid (oxygen consumption for lactic acid and alkalinization of lactates): negative
25. Formation of dehydroxyacetone from glycerol: negative
26. Formation of gluconic acid: positive, at least 0.3 w/v %
27. Formation of 2-ketogluconic acid: weakly positive, 0.1 w/v % of less
28. Formation of 5-ketogluconic acid: negative
29. Formation of 2,5-diketogluconic acid: negative
30. Formation of γ-pyrones from D-glucose: negative
31. Formation of cellulose: negative
32. Growth on Frateur's modified Hoyer medium-ethyl alcohol (vitamins added): negative
33. Growth on Frateur's modified Hoyer medium-glucose (vitamins added): negative
34. Acetic acid requirement: positive, no growth on AE agar plate devoid of acetic acid.
35. Ethyl alcohol requirement: positive, no growth on AE agar plate devoid of ethyl alcohol
36. Glucose requirement: positive, no growth on AE agar plate devoid of glucose (d) Chemotaxonomic characteristics 1. Cellular fatty acid composition, %:
   14:0—1.3
   16:0—13.9
   17:0—trace (less than 1.0)
   18:0—5.4
   16:1—1.0
   18:1—65.5
   20H-14—4.8
   30H-14—trace
   20H-16—7.3
2. Ubiquinone system: $Q_{10}$
3. Guanine plus cytosine content of DNA, determined by the thermal denaturation method: 57.9 mole %
4. DNA homology with affinitive acetic acid bacteria of which the ubiquinone system is $Q_{10}$ or $Q_{10}(Q_9)$, determined by the membrane filter method:
   *Gluconobacter oxydans* subsp. *oxydans* ATCC 19357: 17%
   *Acetobacter aceti* subsp. *xylinum* IFO 3288: 39%
   *Acetobacter aceti* subsp. *liquefaciens* IAM 1834: 11%

As is described above, the bacterial species of the present invention was gram-negative, obligatory aerobic and acidophilic rod which oxidize ethylalcohol to acetic acid, and belongs to the genus Acetobacter or the genus Gluconobacter, which are generally referred to as acetic acid bacteria, according to Bergey's Manual of Determinative Bacteriology, 8th ed., 1974.

The new strain of the present invention has very high resistance to acetic acid and the ability to produce acetic acid, although said strain shows negative results for overoxidation of ethyl alcohol, assimilation of acetic acid, decomposition of acetic acid, assimilation of lactic acid and decomposition of lactic acid. Thus, the new strain of the present invention has an intermediate phenotypic characteristic between those of the genus Acetobacter and the genus Gluconobacter. The strain of the present invention requires more than 4 w/v % of acetic acid as a component for growth medium, and grows at a pH of 2.2–3.5.

As for the cellular fatty acids of this strain, it contains straight-chain unsaturated acid of $C_{18:1}$ as a major constituent and 1.3% of straight-chain saturated acid of $C_{14:0}$ as a minor constituent. The ubiquinone system thereof is $Q_{10}$, and guanine plus cytosine content (GC content) of DNA was determined to be 57.9 mole %.

It is known from the description in (a) The Journal of General and Applied Microbiology, volume 15, pages 181 to 196 (1969) and (b) the same journal, volume 22, pages 285 to 292 (1976) that acetic acid bacteria containing $Q_{10}$ as a major constituent of ubiquinone includes all species of the genus Gluconobacter and *Acetobacter*

*aceti* subsp. *xylinum* and *Acetobacter aceti* subsp. *liquefaciens* belonging to the genus Acetobacter (these names are according to the nomenclature in Bargey's Manual of Determinative Bacteriology, 8th ed. and Approved Lists of Bacterial Names appearing in International Journal of Systematic Bacteriology, volume 30, pages 225 to 420 (1980)). The former of these two species is named *Acetobacter xylinum* or *Acetobacter xylinum* subsp. *xylinum* in the literatures (a) and (b), respectively, and the latter species is named in the literatures (a) and (b) as a peritrichously flagellated intermediate strain or *Acetobacter xylinum* subsp. *liquefaciens*, respectively. A bacteriological comparison of MH-24 was performed with the preserved strains of these species including the type strains which are described in Approved Lists of Bacterial Names and ubiquinone system thereof, namely $Q_{10}$ or $Q_{10}$ (Qg), released by depositories including ATCC, IFO and IAM. It was determined that MH-24 is definitely distinguished from these preserved strains as is shown in Table 1 below. The distinctions are apparent from the differences that MH-24 alone required at least 4 w/v % of acetic acid as an ingredient of the culture medium for growth and grows only at a state of pH of 3.5 or less and that MH-24 required ethyl alcohol for growth and was inactive for the formation of dihydroxyacetone from glycerol and for the formation of 5-ketogluconic acid. MH-24 was also distinguished from *Acetobacter aceti* subsp. *xylinum* IFO 3288 and *Acetobacter aceti* subsp. *liquefaciens* IAM 1834 belonging to the genus Acetobacter by the absence of the activities for overoxidation of ethyl alcohol, assimilation of acetic acid, decomposition of acetic acid, assimilation of lactic acid and decomposition of lactic acid; from *Gluconobacter oxydans* subsp. *oxydans* ATCC 19357, *Gluconobacter oxydans* subsp. *suboxydans* IFO 3990, *Gluconobacter oxydans* subsp. *industrius* IFO 3260, *Gluconobacter oxydans* subsp. *melanogenes* IFO 3293 and *Gluconobacter oxydans* subsp. *sphaericus* IFO 12467 belonging to the genus Gluconobacter in containing a straight chain saturated acid of $C_{14:0}$ as one of the cellular fatty acids; from *Gluconobacter oxydans* subsp. *melanogenes* IFO 3293, *Gluconobacter oxydans* subsp. *sphaericus* IFO 12467 and *Acetobacter aceti* subsp. *liquefaciens* IAM 1834 in the absence of the activities for the formation of brown pigment, 2,5-diketogluconic acid and γ-pyrones from glucose; from *Gluconobacter oxydans* subsp. *sphaericus* IFO 12467 in the cell shape; and from *Acetobacter aceti* subsp. *xylinum* IFO 3288 in the absence of activity for the formation of cellulose. With respect to the GC content of the DNA, in addition, the value in MH-24 was 57.9% which was clearly different from the corresponding values of at least 60% in six of the referred strains excepting *Gluconobacter oxydans* subsp. *industrius* IFO 3260. A novel genus of acetic acid bacteria named Frateuria has been proposed in International Journal of Systematic Bacteriology, volume 30, pages 547 to 556 (1980) but NH-24 can be definitely distinguished from this genus because the ubiquinone system thereof is $Q_8$ ($Q_7$) and contains iso-branched chain acid of $C_{15:0}$ as a cellular fatty acid.

Recently, reports suggesting reconsideration of the classification system of Bergey's Manual of Determinative Bacteriology, 8th ed. (1974) were published. Background consideration was made of the taxonomical proposals appearing in recent scientific journals. For example, International Journal of Systematic Bacteriology, volume 33, pages 65 to 81 (1983) proposed to cancel the subdivision of *Gluconobacter oxydans*, and thus the above subspecies are named to *Gluconobacter oxydans*. The Journal of General and Applied Microbiology, volumn 29, pages 417 to 420 (1983) proposed to classify the above-mentioned *Acetobacter aceti* subsp. *xylinum* as *Acetobacter xylinum* as a different species from *Acetobacter aceti*. Further, (a) Systematic and Applied Microbiology, volume 3, pages 338 to 368 (1983) and (b) The Journal of General and Applied Microbiology, volume 29, pages 327 to 333 (1983) proposed to classify the above-mentioned *Acetobacter aceti* subsp. *liquefaciens* as *Acetobacter liquefaciens* as a different species from *Acetobacter aceti*. In the above report (a), a new species named *Acetobacter hansenii* was described. However, the ubiquinone system was not adopted as a taxonomic criterion, and thus there coexist a strain containing $Q_{10}$ as a major constituent of ubiquinone and a strain containing $Q_9$ as a major constituent in the strains which were classified into *Acetobacter hansenii* sp. *nov*. It seems that a taxonomic status of *Acetobacter hansenii* sp. *nov*. should be reconsidered since the ubiquinone system is understood to be effective as a criterion for classifying various microorganisms.

In combination with the above-described background considerations, comparison was made of the DNA homologies between MH-24 and the strains, i.e. *Gluconobacter oxydans* subsp. *oxydans* ATCC 19357 (type strain), *Acetobacter aceti* subsp. *xylinum* IFO 3228 and *Acetobacter aceti* l subsp. *liquefaciens* IAM 1834 (type strain) to find that the values of these referred strains were all 39% or less leading to a conclusion that MH-24 forms an apparently different species from these strains.

In addition to the conclusion derived from the above-described results and considerations that MH-24 is a novel species belonging to the genus Gluconobacter or Acetobacter, the inventors have been led to a final conclusion that the novel species of bacteria of the invention represented by MH-24 belongs to the genus Acetobacter to be given a species name of *Acetobacter altoacetigenes* setting more importance on the chemotaxonomic properties that MH-24 contains the straight chain saturated acid of $C_{14:0}$, which is characteristic of the cellular fatty acids of the genus Acetobacter, which was described in The Journal of General and Applied Microbiology, vol. 27, pages 405–417 (1981), and that the value of the DNA homology between MH-24 and *Gluconobacter oxydans* subsp. *oxydans* ATCC 19357 is only 17% while the value between MH-24 and *Acetobacter aceti* subsp. *xylinum* IFO 3288 is 39% than on the physiological properties including the absence of the activities for the overoxidation of ethyl alcohol, assimilation of acetic acid, decomposition of acetic acid, assimilation of lactic acid and decomposition of lactic acid.

No special conditions are required in the fermentation production of vinegars such as white vinegar using the novel bacterial species of the invention. Thus, the prior art processes can be used, except that the inoculant is an isolation culture of the bacterium MH-24. The fermentation porcess proceeds with higher stability than in the conventional process without frothing taking place in the course of the fermentation so that the fermentation process control is greatly facilitated. The novel bacterial species of the invention can be used advantageously in the fermentation production of white vinegar with high acetic acid concentration having excellent flavor and taste with a high efficiency and productivity.

The following Examples illustrate the invention in more detail.

EXAMPLE 1

In a Sakaguchi flask of 500 ml capacity were prepared 100 ml of a liquid culture medium containing 0.2 w/v % of yeast extract, 0.3 w/v % of polypeptone, 1.5 w/v % of glucose, 6.5 w/v % of acetic acid and 6.5 V/v % of ethyl alcohol. The medium was sterilized by heating. The culture medium was prepared in 17 flasks in the same manner. After cooling, each of the thus prepared culture media was inoculated with one of the 17 typical strains of acetic acid bacteria including MH-24 as the representative strain of the inventive bacteria. Culture was performed by shaking at 30° C. for 5 days. The strain of MH-24 used in the inoculation was fresh cells grown on an AE agar plate while each of the other 16 strains used in the inoculation were respective fresh cells grown on a slant containing 0.2 w/v % of yeast extract, 0.3 w/v % of polypeptone, 3 w/v % of glucose and 1.5 w/v % of agar.

Table 2 summarizes the growth of the bacteria, final acetic acid concentration and the increment of the acetic acid concentration caused by the fermentation which is obtained by subtracting the initial acetic acid concentration, i.e. 6.5 w/v %, from the final acetic acid concentration to provide the amount of acetic acid produced by the fermentation. As is clear from this table, the growth of the bacteria was noted only when the bacterial strain was MH-24 and the final acetic acid concentration reached 12.5 w/v % to give a production of acetic acid corresponding to 6.0 w/v % increment of the acetic acid concentration.

As is understood from the above-described experimental results, high acidity vinegars can be produced by a fermentation process using the pure culture of MH-24.

EXAMPLE 2

In a fermentation apparatus with agitation and aeration having a capacity of 10 liters, were charged 7.2 liters of a broth containing 6.5 w/v % of acetic acid and 6.5 w/v % of alcohol. The broth was prepared by use of alcohol, water, finished acetic acid fermentation liquid and necessary nutrients for acetic acid bacteria. After sterilization by heating, the broth was agitated with aeration at a rate of 0.1 VVM at a controlled temperature of 30° C. Thereafter, fermentation was started by the inoculation with 0.8 liter of a fermenting seed vinegar of MH-24 (FERM BP-491) prepared in the same manner as in Example 1, in which the acetic acid concentration had reached 8 w/v %. When the acetic acid concentration increased and reached 11.5 w/v %, the fermenting broth was discharged from the fermentation apparatus without interruption of the agitation and aeration leaving a portion of about 4 liters. Then about 4 liters of a starting broth, which had been prepared by use of alcohol, water, finished acetic acid fermentation liquid and nutrients for the acetic acid bacteria to have an acetic acid concentration of 1 w/v % ad an alcohol concentration of 4.5 w/v %, were added thereto so that the acetic acid concentration and the alcohol concentration were brought to about 6.3 w/v % and about 2 v/v %, respectively, of the broth contained in the apparatus after the re-filling with the starting broth.

While the acetic acid fermentation was accompanied by an increase of the acetic acid concentration and decrease of the alcohol concentration, the alcohol concentration of the broth contained in the apparatus with agitation and aeration was maintained at about 2% by the portion-wise addition of a solution containing 50 w/v % of alcohol and the nutrient source of the same composition as in the starting broth. When the total concentration had reached about 15.5% and sufficient to provide an acetic acid concentration of 15 w/v %, the feed of the above-mentioned alcoholic solution was interrupted and the fermentation was further continued to produce an acetic acid fermentation liquid, namely, a wite vinegar, having an acetic acid concentration of 15 w/v % and an alcohol concentration of 0.3 w/v %.

The white vinegar of high acetic acid concentration was a high-quality vinegar product having absolutely no offensive taste and odor.

TABLE 1

| Properties | MH-24 | Gluconobacter oxydans subsp. oxydans ATCC 19357 | Gluconobacter oxydans subsp. suboxydans IFO 3990 | Gluconobacter oxydans subsp. industrius IFO 3260 | Gluconobacter oxydans subsp. melanogenes IFO 3293 | Gluconobacter oxydans subsp. sphaericus IFO 12467 | Acetobacter aceti subsp. xylinum IFO 3288 | Acetobacter aceti subsp. liquefaciens IAM 1834 |
|---|---|---|---|---|---|---|---|---|
| Shape | Rod | Rod | Rod | Rod | Rod | Sphere | Rod | Rod |
| Overoxidation of Ethyl Alcohol | − | − | − | − | − | − | + | + |
| Assimilation of Acetic Acid | − | − | − | − | − | − | + | + |
| Decomposition of Acetic Acid | − | − | − | − | − | − | + | + |
| Assimilation of Lactic Acid | − | − | − | − | − | − | + | + |
| Decomposition of Lactic Acid | − | − | − | − | − | − | + | + |
| Formation of 5-Ketogluconic Acid | − | + | + | + | + | + | + | + |
| Formation of 2,5-Diketogluconic Acid | − | − | − | − | + | + | − | + |
| Formation of γ-Pyrones from Glucose | − | − | − | − | + | + | − | + |
| Formation of Brown Pigment | − | − | − | − | + | + | − | + |
| Formation of Cellulose | − | − | − | − | − | − | + | − |
| Formation of Dihydroxyacetone from Glycerin | − | + | + | + | + | + | + | + |
| Range of Acetic Acid Concentration for Growth (%(W/V)) | 4~10 | 0~0.5 | 0~0.5 | 0~0.5 | 0~0.5 | 0~0.5 | 0~1 | 0~0.5 |
| Acetic Acid Requirement | + | − | − | − | − | − | − | − |
| Ethyl Alcohol Requirement | + | − | − | − | − | − | − | − |

TABLE 1-continued

| Properties | Strain | | | | | | | |
|---|---|---|---|---|---|---|---|---|
| | MH-24 | Gluconobacter oxydans subsp. oxydans ATCC 19357 | Gluconobacter oxydans subsp. suboxydans IFO 3990 | Gluconobacter oxydans subsp. industrius IFO 3260 | Gluconobactor oxydans subsp. melanogenes IFO 3293 | Gluconobacter oxydans subsp. sphaericus IFO 12467 | Acetobacter aceti subsp. xylinum IFO 3288 | Acetobacter aceti subsp. liquefaciens IAM 1834 |
| Growth on Medium of pH 4~7 | − | + | + | + | + | + | + | + |
| Ubiquinone System | $Q_{10}$ | $Q_{10}$ | $Q_{10}$ | $Q_{10}$ | $Q_{10}$ | $Q_{10}$ | $Q_{10}$ | $Q_{10}$ ($Q_9$) |
| $C_{1410}$ Content of Cellular Fatty Acid (%)[*1] | 1.3 | ND | ND | ND | ND | ND | 4.4 | 7.5 |
| GC Content of DNA (mol %)[*1] | 57.9 | 60.6 | 60.6 | 56.9 | 62.0 | 61.5 | 62.5 | 64.5 |
| DNA Homology (%) | 100 | 17 | * | * | * | * | 39 | 11 |

+: Positive, −: Negative, ND: Not Detected, *: Not Examined
[*1] Cited from the disclosure of "The Journal of General and Applied Microbiology" 27, 405~417, 465~475 (1981) except for strain MH-24

TABLE 2

| Strain | Growth | Acetic Acid Production (%(W/V)) | Final Acetic Acid Concentration (%(W/V)) |
|---|---|---|---|
| MH-24 | + | 6.0 | 12.5 |
| Gluconobacter oxydans subsp. oxydans ATCC 19357 | − | 0 | 6.5 |
| Gluconobacter oxydans subsp. suboxydans IFO 3990 | − | 0 | 6.5 |
| Gluconobacter oxydans subsp. industrius IFO 3260 | − | 0 | 6.5 |
| Gluconobacter oxydans subsp. melanogenes IFO 3293 | − | 0 | 6.5 |
| Gluconobacter oxydans subsp. sphaericus IFO 12467 | − | 0 | 6.5 |
| Acetobacter aceti subsp. aceti ATCC 15973 | − | 0 | 6.5 |
| Acetobacter aceti subsp. orleanensis IFO 13752 | − | 0 | 6.5 |
| Acetobacter aceti subsp. xylinum IFO 3288 | − | 0 | 6.5 |
| Acetobacter aceti subsp. liquefaciens IAM 1834 | − | 0 | 6.5 |
| Acetobacter pasteurianus subsp. pasteurianus IFO 3233 | − | 0 | 6.5 |
| Acetobacter pasteurianus subsp. lovaniensis IFO 13753 | − | 0 | 6.5 |
| Acetobacter pasteurianus subsp. estunensis IFO 13751 | − | 0 | 6.5 |
| Acetobacter pasteurianus subsp. ascendens IFO 3188 | − | 0 | 6.5 |
| Acetobacter pasteurianus subsp. paradoxus IFO 13754 | − | 0 | 6.5 |
| Acetobacter peroxydans IFO 13755 | − | 0 | 6.5 |
| Frateria aurantia IFO 3245 | − | 0 | 6.5 |

+ : Positive
− : Negative

What is claimed is:

1. A biologically pure culture consisting of the acetic acid bacterium, *Acetobacter altoacetigenes* MH-24 (FERM BP-491) which requires more than 4 w/v % of acetic acid as a component for growth medium, and grows only at a pH of 3.5 or less.

* * * * *